(12) United States Patent
Tischler et al.

(10) Patent No.: US 9,921,162 B2
(45) Date of Patent: Mar. 20, 2018

(54) DETERMINATION OF A FUNGAL INFECTION OF A PLANT BY CHLOROPHYLL FLUORESCENCE INDUCED BY DIFFERENT EXCITATION WAVELENGTHS

(71) Applicant: BASF SE, Ludwigshafen (DE)

(72) Inventors: Ylva Tischler, Kiel (DE); Eberhard Hartung, Kiel (DE); Eiko Thiessen, Kiel (DE)

( * ) Notice: Subject to any disclaimer, the term of this patent is extended or adjusted under 35 U.S.C. 154(b) by 0 days.

(21) Appl. No.: 15/105,056

(22) PCT Filed: Dec. 17, 2014

(86) PCT No.: PCT/EP2014/078198
§ 371 (c)(1),
(2) Date: Jun. 16, 2016

(87) PCT Pub. No.: WO2015/091632
PCT Pub. Date: Jun. 25, 2015

(65) Prior Publication Data
US 2016/0349180 A1  Dec. 1, 2016

(30) Foreign Application Priority Data

Dec. 18, 2013 (EP) .................................... 13198050

(51) Int. Cl.
*F21V 9/16* (2006.01)
*G01N 21/64* (2006.01)
(Continued)

(52) U.S. Cl.
CPC ..... *G01N 21/6486* (2013.01); *G01N 33/0098* (2013.01); *G01N 2021/635* (2013.01);
(Continued)

(58) Field of Classification Search
CPC ....... G01N 21/6486; G01N 2021/6419; G01N 2021/6421; G01N 2021/8466;
(Continued)

(56) References Cited

U.S. PATENT DOCUMENTS 5,412,219 A * 5/1995 Chappelle .............. G01N 21/64
250/253
6,366,681 B1 4/2002 Hutchins
(Continued)

OTHER PUBLICATIONS

Pfündel et al., "Investigating UV Screening in Leaves by Two Different Types of Portable UV Fluorimeters Reveals in vivo Screening by Anthocyanins and Carotenoids," Photosynth Res, vol. 93, (2007), pp. 205-221.
(Continued)

*Primary Examiner* — Taeho Jo
(74) *Attorney, Agent, or Firm* — Brinks Gilson & Lione

(57) ABSTRACT

The present invention relates to a method for determining a fungal infection of a plant—The method comprises: emitting excitation radiation by one or more radiation sources to the plant, said radiation comprising first excitation wavelengths being within the absorption band of a compound whose content in the plant is affected by a fungal infection, in particular a phenolic compound, and second excitation wavelengths being outside the absorption band of said compound, thereby inducing chlorophyll fluorescence; detecting chlorophyll fluorescence radiation from the plant; and obtaining a value being indicative for the fungal infection of the plant, said value is dependent from the detected chlorophyll fluorescence radiation induced by excitation radiation of the first excitation wavelengths and the detected chlorophyll fluorescence radiation induced by excitation radiation of the second excitation wavelengths. Moreover, the present invention relates to a detection device, in par-
(Continued)

ticular a mobile detection device, for carrying out this method.

20 Claims, 5 Drawing Sheets

(51) Int. Cl.
    *G01N 33/00*     (2006.01)
    *G01N 21/63*     (2006.01)

(52) U.S. Cl.
    CPC ............... *G01N 2021/6419* (2013.01); *G01N 2201/062* (2013.01)

(58) Field of Classification Search
    CPC ... G01N 2201/0221; G01N 2021/1736; G01N 2021/3148; G01N 2021/3155; G01N 2021/3181; G01N 21/3151; G01N 21/6456; G01N 21/84
    USPC ...................................................... 250/459.1
    See application file for complete search history.

(56) References Cited

U.S. PATENT DOCUMENTS

| | | | |
|---|---|---|---|
| 6,563,122 B1 * | 5/2003 | Ludeker | G01N 21/6456 250/458.1 |
| 6,855,933 B2 | 2/2005 | Stone et al. | |
| 6,914,250 B2 * | 7/2005 | Seville | G01N 21/6428 250/458.1 |
| 7,408,145 B2 | 8/2008 | Holland | |
| 7,715,013 B2 | 5/2010 | Glaser et al. | |
| 7,910,876 B2 | 3/2011 | Kumagai et al. | |
| 8,179,533 B2 | 5/2012 | Alameh | |
| 2004/0033555 A1 * | 2/2004 | Anderson | C12Q 1/18 435/34 |
| 2005/0072935 A1 * | 4/2005 | Lussier | G01N 21/6456 250/458.1 |
| 2005/0098713 A1 * | 5/2005 | Holland | G01J 3/10 250/221 |
| 2008/0239293 A1 * | 10/2008 | Fuchigami | G01N 21/3151 356/73 |
| 2010/0181496 A1 * | 7/2010 | Moise | G01N 21/645 250/459.1 |
| 2010/0184117 A1 | 7/2010 | Cerovic et al. | |
| 2010/0279332 A1 * | 11/2010 | Cerovic | G01N 21/3151 435/29 |
| 2011/0186752 A1 * | 8/2011 | Moise | G01J 3/4406 250/459.1 |
| 2011/0273705 A1 * | 11/2011 | Rao | G01N 21/532 356/222 |
| 2012/0018356 A1 * | 1/2012 | Jalink | G01N 21/6408 209/576 |
| 2012/0115215 A1 * | 5/2012 | Eckles | F21V 7/05 435/288.7 |
| 2013/0255150 A1 * | 10/2013 | Karpinski | A01G 7/045 47/58.1 LS |
| 2013/0256561 A1 * | 10/2013 | Greenbaum | G01N 21/6486 250/459.1 |
| 2015/0313092 A1 * | 11/2015 | Pocock | A01G 7/045 47/58.1 LS |

OTHER PUBLICATIONS

Qawasmeh et al., "Influence of Fungal Endophyte Infection on Phenolic Content and Antioxidant Activity in Grasses: Interaction between *Lolium perenne* and Different Strains of *Neotyphodium lolii*," J. Agric. Food Chem., vol. 60, (2012), pp. 3381-3388.

International Search Report, issued in PCT/EP2014/078198, dated Apr. 8, 2015.

International Preliminary Report on Patentability, issued in PCT/EP2014/078198, dated Apr. 5, 2016.

* cited by examiner

US 9,921,162 B2

DETERMINATION OF A FUNGAL INFECTION OF A PLANT BY CHLOROPHYLL FLUORESCENCE INDUCED BY DIFFERENT EXCITATION WAVELENGTHS

This application is a National Stage application of International Application No. PCT/EP2014/078198, filed Dec. 17, 2014. This application also claims priority under 35 U.S.C. § 119 to European Patent Application No. 13198050.0, filed Dec. 18, 2013.

BACKGROUND OF INVENTION

The present invention relates to a method and a detecting device for determining a fungal infection of a plant.

It is known that the health of plants can be assessed by detecting and analyzing the chlorophyll content in plant leaves. If the health of a plant is affected the chlorophyll content in the leaves of this plant is reduced. This reduction can be detected by the light that is reflected by the leaves of the plant.

U.S. Pat. No. 6,366,681 B1 describes a method for generating a chlorophyll-based health map for a geographic area. According to this method, a satellite, and airplane or another elevated device passes over a farmer's field and an imaging device records a multi-spectral digital image. Based on this multi-spectral digital image the chlorophyll content of the leaves of the farmer's field is analyzed, and a chlorophyll-based health map is created.

U.S. Pat. No. 6,855,933 B2 describes an optical spectral reflectance sensor and controller. The sensor obtains the reflectance properties of a plant. By observing the reflected light at particular wavelengths and the intensity of the light source at the same wavelengths, the expected crop yield with a particular level of available nitrogen and the maximum crop yield, if an ideal amount of nitrogen fertilizer is added, are calculated.

U.S. Pat. No. 7,715,013 B2 describes an optical system for plant characterization. In particular, a stressor of a plant is determined. In the method reflected solar energy from a plant surface is collected, the collected solar energy is formed into a multi-band image, and this image is analyzed.

U.S. Pat. No. 7,408,145 B2 describes a light sensing instrument with a modulated polychromatic source. By this apparatus the plant status is assessed using biophysical and biochemical properties of the plant remotely sensed. A single polychromatic emitter provides coincident light beams. A detector array detects portions of this polychromatic light beam reflected by a surface area and provides a signal indicative of whether the detected light was reflected by a plant or by some non-plant object, such as soil. Based on this signal, the plant may be sprayed by a herbicide, or a fertilizer is applied.

U.S. Pat. No. 7,910,876 B2 describes a plant sensor that includes a light source section having first and second light emitters configured to irradiate first and second measuring light toward an object to be measured and a light receiver configured to receive reflected light from the object to be measured. Based on output light-receiving signals information regarding a growing condition of the object to be measured is obtained.

Further, U.S. Pat. No. 8,179,533 B2 describes a sensing system and method for discriminating plant matter. The sensing system comprises a light source having three or more distinct wavelengths for illuminating a plurality of distinct areas in a field of view, a sensor for measuring the reflectance of distinct areas at each of the distinct wavelengths, and an identifier for identifying at least one object in the field of view from the measured reflectance at each of the wavelengths. This system may be used to detect pests, such as insects.

The method and systems described above have the disadvantage that a disease of a plant such as a fungal infection may only be detected if the disease has affected the plants so that the reflection properties of the plant have changed.

Finally, US 2010/0184117 A1 describes a method for determining the content of a non-fluorescent chromophorous first compound, in a biological tissue including a fluorescent chromophorous second compound. The method includes the emission of a first reference optical radiation, and a second measurement optical radiation, each chosen so as to induce a fluorescence radiation of the second compound, each of the first and second radiations being partially absorbed by the first compound. The fluorescence radiations induced by each of the first and second radiations are measured and the content of the first compound in the tissue is determined from the measurement. Moreover, US 2011/0186752 A1 describes a method for determining the ratio of the contents of chlorophyll and of a chromophorous compound that is non-fluorescent in the band of chlorophyll fluorescence in a plant tissue, without determining the contents.

SUMMARY OF INVENTION

It is the object of the present invention to provide a method and a detecting device that can detect a fungal infection of a plant as early as possible.

According to the invention, this object has been achieved by a method as defined in claim 1 and a detecting device as defined in claim 12. Further features of this method and device are defined in the dependent claims.

Accordingly, the method for determining a fungal infection of a plant according to the present invention comprises the following steps:

Excitation radiation is emitted by one or more radiation sources to the plant. The radiation comprises first excitation wavelengths being within the absorption band of a compound whose content in the plant is affected by a fungal infection and second excitation wavelengths being outside the absorption band of said compound, thereby inducing chlorophyll fluorescence, in particular by both radiation wavelengths. The chlorophyll fluorescence radiation from the plant is detected. Thereafter, a value being indicative for the fungal infection of the plant is obtained. This value is dependent on the detected chlorophyll fluorescence radiation induced by excitation radiation of the first excitation wavelengths and the detected chlorophyll fluorescence radiation induced by excitation radiation of the second excitation wavelengths.

The radiation source or the radiation sources that are used in accordance with the present invention may emit electromagnetic waves in a broad or narrow wavelength spectrum. The emission may only comprise the first and second excitation wavelengths. Furthermore, the emission may comprise not only the first and second excitation wavelengths but also other wavelengths of the electromagnetic spectrum.

According to one embodiment, the emitted excitation radiation comprises only the first and second excitation wavelengths as defined above. According to another embodiment, the plant is illuminated by broad-spectrum electromagnetic radiation. In this case, according to one embodiment, said emitting excitation radiation includes illuminating electromagnetic radiation to the plant and filtering said illuminated electromagnetic radiation to said first excitation wavelengths being within the absorption band of the compound whose content in the plant is affected by the fungal infection and to said second excitation wavelength being outside the absorption band of said compound.

According to a further embodiment, instead of filtering the illuminated electromagnetic radiation a hyperspectral sensor may be used, and only the bands with the required wavelengths are used for the analysis. Therefore, according to a further embodiment, said emitting excitation radiation includes illuminating electromagnetic radiation to the plant, and said detecting chlorophyll fluorescence radiation from the plant includes detecting chlorophyll fluorescence radiation induced by excitation radiation of the first excitation wavelengths and detecting chlorophyll fluorescence radiation induced by excitation radiation of the second excitation wavelength. The hyperspectral sensor uses hyperspectral imaging in which information from across the electromagnetic spectrum is collected and processed. The detected images are divided into bands that may be processed separately. In other words, the hyperspectral sensor collects information as a set of images, wherein each image represents a narrow wavelength range of the electromagnetic spectrum.

According to one embodiment, the compound whose content in the plant is affected by the fungal infection is a phenolic compound.

The invention utilizes that a fungal infection of a plant affects the content of a specific compound, in particular of phenolic compounds in the plant. Such change of the phenolic compound content arises before the chlorophyll concentration in the plant tissue is reduced because of the fungal infection. Thus, using excitation radiation having a wavelength within the absorption band and excitation radiation having a wavelength outside the absorption band of a phenolic compound will lead to a change of chlorophyll fluorescence radiation, if the content of the phenolic compound changes. The phenolic compound will partly absorb excitation wavelengths within the absorption band of the phenolic compound, whereas excitation wavelengths being outside the absorption band of the phenolic compound will not be absorbed. Therefore, the chlorophyll fluorescence radiation induced by the first excitation wavelengths decreases with an increase of the absorption of the excitation radiation. A change of the content of the phenolic compound will lead to a change of the value that is dependent on the chlorophyll fluorescence radiation used by excitation radiation of the first excitation wavelengths being within the absorption band of the phenolic compound. Thus, the value is indicative of the fungal infection of the plant, although a reduction of the chlorophyll concentration in the plant tissue that could be detected by light reflection has not occurred yet. Therefore, the method of the present invention can detect a fungal infection of a plant earlier than a conventional method using images of reflected radiation.

In contrast to a visible reflection of light by the plant leaves that is mainly influenced by the chlorophyll concentration in the plant tissue, the chlorophyll fluorescence radiation comprises also information on changes induced by fungal infection of the plant before such changes are visible. Therefore, the method of the present invention can determine a fungal infection before symptoms are visible. In the method of the present invention the fungus is not detected directly. Instead, compounds of the plant are detected whose concentration is changed by the fungal infection of the plant. Furthermore, the change of the photosynthesis of the affected leaves may be determined. The concentration change is determined by fluorescence spectroscopy by analyzing excitation or emission spectra. The activity of photosynthesis may be measured as kinetic of the variable chlorophyll fluorescence.

The first and second excitation wavelengths are chosen with respect to the absorption band of the compound, in particular a phenolic compound. In particular the phenolic compound is a polyphenol. Relevant polyphenols in plants are, in particular, flavonoids, anthocyans, procyanides, benzoic acid derivatives, cinnamic acid derivatives and stilbene derivatives. For measurements on wheat plants in particular cis and trans ferulic acid, cis and trans coumaric acid, vanillin and syringa acid, as well as smaller amounts of p-hydroxybenzaldehyde, p-hydroxybenzoic acid and vanillic acid are relevant.

For the chlorophyll fluorescence measurement it is not necessarily useful to apply exactly a wavelength from the absorption maximums of polyphenols for excitation: although the biggest changes in absorption behavior for changes of polyphenol content occur if the excitation is carried out at the absorption maxima, if such a excitation wavelength is used, the absorption may be so high that little or no radiation may reach the chlorophyll to excite it. In such a case no chlorophyll fluorescence can be measured, let alone any changes of chlorophyll fluorescence when the polyphenol content changes due to an infection. In summary, the choice of the ultraviolet excitation wavelength is a compromise between polyphenol absorption, the yield of chlorophyll fluorescence, and the power efficiency of available radiation sources in this ultraviolet range.

Therefore, according to one embodiment, the first excitation wavelength is chosen to be within the absorption band of the compound, in particular the phenolic compound, but not at the absorption maximum of the compound, in particular the phenolic compound.

In one embodiment the value that is indicative of the fungal infection of the plant is dependent on the ratio of the detected chlorophyll fluorescence radiation induced by excitation radiation of the first excitation wavelengths and the detected chlorophyll fluorescence radiation induced by excitation radiation of the second excitation wavelengths. In particular, the value is the quotient of the fluorescence radiation induced by excitation radiation of the second excitation wavelengths divided by the fluorescence radiation induced by excitation radiation of the first excitation wavelengths. Advantageously, the fluorescence radiation used by excitation radiation of the second excitation wavelengths that are outside the absorption band of the compounds, in particular the phenolic compounds, is used as reference for scaling. By means of this scaling, the value will become independent of the measurement distance, the geometry of the plant, and the concentration of chlorophyll in the plant tissue.

Pure ferulic acid has absorption maxima at about 235 nm and at about 325 nm, and the absorption disappears at about 400 nm. Pure coumaric acid has absorption maxima at about 230 nm and 280 nm and shows absorption up to about 350 nm. In dissolved form, and even more when embedded in a plant cell, these absorption bands shift strongly, depending on pH, even by 30 nm.

Therefore, the first excitation wavelengths are, in particular, in a range from 200 nm to 400 nm, and the second excitation wavelengths are in a range from 450 nm to 650 nm. Preferably, the first excitation wavelengths are in a range from 350 nm to 400 nm, and more preferably, excitation radiation of 365 nm or 395 nm is used.

In a further embodiment the chlorophyll fluorescence radiation from the plant is detected for at least first and second measurement wavelengths (emission wavelengths of chlorophyll), said first and second measurement wavelengths being different. For example, the first measurement wavelength is between 670 nm and 700 nm, and the second measurement wavelength is between 715 nm and 745 nm. Preferably, in this case the detected fluorescence radiation is analyzed at the first measurement wavelength relative to the detected chlorophyll fluorescence radiation at the second measurement wavelength, thereby determining the reduction of chlorophyll concentration in the plant.

According to this embodiment, not only a change of the content of a phenolic compound induced by a fungal infection is determined, but also a change of the chlorophyll concentration in the plant tissue. The reduction of the chlorophyll concentration will take place after the change of the content of the phenolic compound. However, according to the method of the present invention, both effects of a fungal infection may be determined by only one measurement using the fluorescence radiation of chlorophyll. Therefore, also a later stage of the fungal infection may be detected. It is not necessary to use another detector for determining visible changes of the leaves of the plants induced by the reduction of the chlorophyll concentration. Conventionally for this reduction of the chlorophyll concentration a detector for detecting reflected light is used.

According to a further embodiment, the excitation radiation comprises at least four different discrete excitation wavelengths. In this case the value that is indicative of the fungal infection of the plant is dependent on the detected chlorophyll fluorescence radiations induced by excitation radiation of said at least four discrete excitation wavelengths. For example, the first excitation wavelength is between 360 nm and 400 nm, the second excitation wavelength is between 450 nm and 480 nm, the third excitation wavelength is between 510 nm and 530 nm, and the fourth excitation wavelength is between 585 nm and 630 nm.

It is noted that some of the excitation wavelengths are outside the absorption band of the compound, in particular the phenolic compound. However, it has turned out that such wavelengths may not only be used for scaling. Surprisingly, it turned out that also chlorophyll fluorescence radiation induced by wavelengths outside the absorption band of the phenolic compound may point to a fungal infection of the plant. Excitation wavelengths of longer wavelengths than the absorption band of the phenolic compound also change the chlorophyll fluorescence radiation of a plant having a fungal infection.

According to one embodiment, the excitation radiation irradiates one or more leaves of the plant. In particular, the plant is irradiated from a distance larger than 10 cm and less than 10 m, in particular the distance is larger than 50 cm and less than 1 m. In this case the method can be implemented by mounting a detector on a vehicle like a tractor, moving on a field with the plants to be determined. In this case, the measured area is large enough to determine the degree of fungal infections of the plants when the tractor moves over the field, even if ambient light also illuminates the plants. In this case, advantageously the application of a fungicide may be carried out at the same time, depending on the determined value for the fungal infection of the plants. Advantageously, the value determined by the method of the present invention is rarely influenced by disturbances like the measurement geometry or sunlight.

According to a further embodiment, the plant is a grass, in particular grain, e.g. wheat. According to a further embodiment, the plant may have no or just little amounts of anthocyanins.

The present invention further provides a detecting device for determining a fungal infection of a plant, comprising one or more radiation sources for emitting excitation radiation to the plant, said radiation comprising first excitation wavelengths being within the absorption band of a compound whose content in the plant is affected by a fungal infection, and second excitation wavelengths being outside the absorption band of said compound, thereby inducing chlorophyll fluorescence. Furthermore, the detecting device comprises a detector for detecting chlorophyll fluorescence radiation from the plant. Moreover, the detecting device comprises an analyzing unit coupled with the detector for obtaining a value being indicative of the fungal infection of the plant. This analyzing unit is adapted to calculate said value in dependence on the detected chlorophyll fluorescence radiation induced by excitation radiation of the first excitation wavelengths and the detected chlorophyll fluorescence radiation induced by excitation radiation of the second excitation wavelengths.

Said compound whose content in the plant is affected by the fungal infection is, in particular, a phenolic compound.

The detecting device is particularly adapted to carry out a method of the present invention as described above. It provides, therefore, the same advantages as the method of the present invention.

According to one embodiment of the invention, said detecting device is a mobile detecting device. The detecting device of the present invention is mobile in the sense that it may be carried by a vehicle, in particular a land vehicle like a tractor, and may move over the field on which the plants to be determined are planted. According to one embodiment of the invention, the detecting device is not part of an aeroplane or a satellite.

According to another embodiment, the detecting device is part of a flying object, like an aeroplane, a drone, a helicopter, or a satellite.

According to a further embodiment, the detecting device is not mobile and is fixed on the plant field.

According to an embodiment of the detecting device, the detector comprises one or more optical elements having an entrance pupil at infinity. In particular, the optical elements are arranged to form a telecentric lense system. This provision provides the advantage that the measurement area on the plants is rather large, and that the measurement distance is also large enough so that the detection can be carried out from a tractor moving over the field. For example, the measurement area has a diameter in the range of 5 cm to 50 cm, in particular from 8 cm to 15 cm. The measurement distance may particularly be larger than 10 cm, in particular about or larger than 50 cm. However, the measurement distance is less than 10 m, in particular less than 1 m.

According to an embodiment of the detecting device, the radiation sources are semiconductor diodes which may also be called light-emitting diodes although the emitted radiation is not necessarily visible light. In particular, the light-emitting diodes emit at least four different discrete excitation wavelengths. Preferably, at least four different types of light-emitting diodes are provided, each type of the light-emitting diodes emit light at a discrete wavelength. Using light-emitting diodes has the advantage that the band width of the emitted wavelength is rather narrow, and the diodes are available at low cost and have a long lifetime.

In a further embodiment, the detector is adapted to detect the chlorophyll fluorescence radiation for at least a first and a second measurement wavelength, said first and second measurement wavelengths being different. As described above, the measurement of the chlorophyll fluorescence radiation at two different wavelengths can be analyzed so that not only the change of the concentration or content of the phenolic compound is determined but also a potential reduction of the chlorophyll concentration in the plant tissue.

Moreover, the present invention is directed to an apparatus for determining a fungal infection of a plant comprising the detecting device as mentioned above. In particular, the apparatus is a vehicle. In this case, vehicles shall include land vehicles like tractors as well as trailers for vehicles having a driving motor, flying objects like aeroplanes, helicopters or drones as well as satellites.

According to a further embodiment, the apparatus is fixed on the plant field. For example, the detecting device may be mounted to a tripod. The tripod with the detecting device may be left in the field during the season. Furthermore, the detecting device may be added to a fixed mount in order to monitor the plant all season.

BRIEF DESCRIPTION OF THE DRAWINGS

Embodiments of the present invention are now described with reference to the figures.

DETAILED DESCRIPTION OF INVENTION

Figure 1:
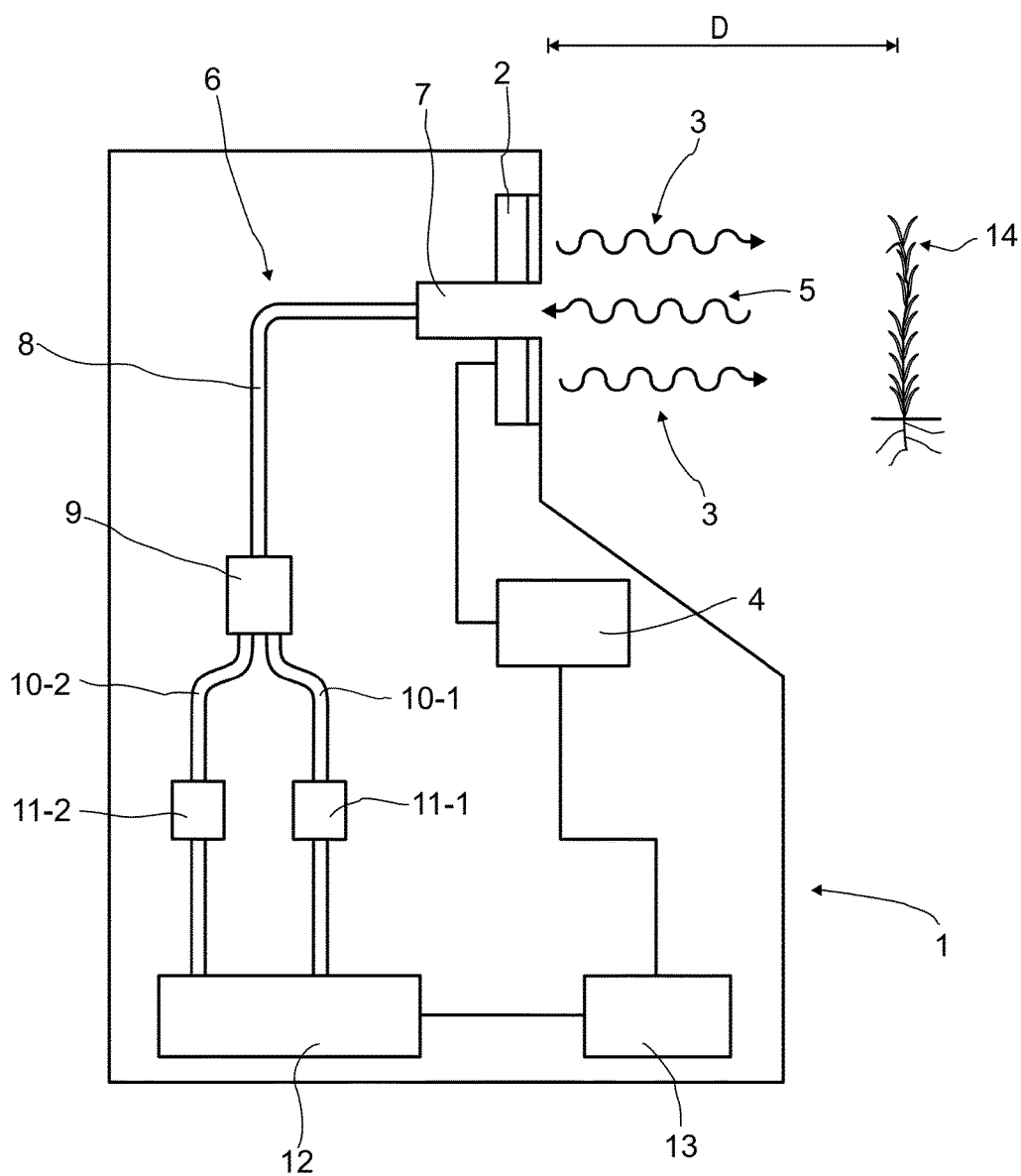
FIG. 1 shows schematically the structure of an embodiment of the mobile detecting device according to the present invention.

In the following, the embodiment of the mobile detecting device is described with reference to FIGS. 1 to 3:

The mobile detection device 1 comprises a light-emitting unit 2. The light-emitting unit 2 is adapted to emit excitation radiation 3 in the direction of a plant 14 of which a potential fungal infection shall be determined. In particular, the excitation radiation 3 of the light-emitting unit 2 irradiates one or more leaves of the plant 14. The distance D between the light-emitting unit 2 and the plant 14 may be in the range of 30 cm to 1 m. The diameter of the radiated spot on the leaves of the plant 14 is approximately 10 cm.

Figure 2:
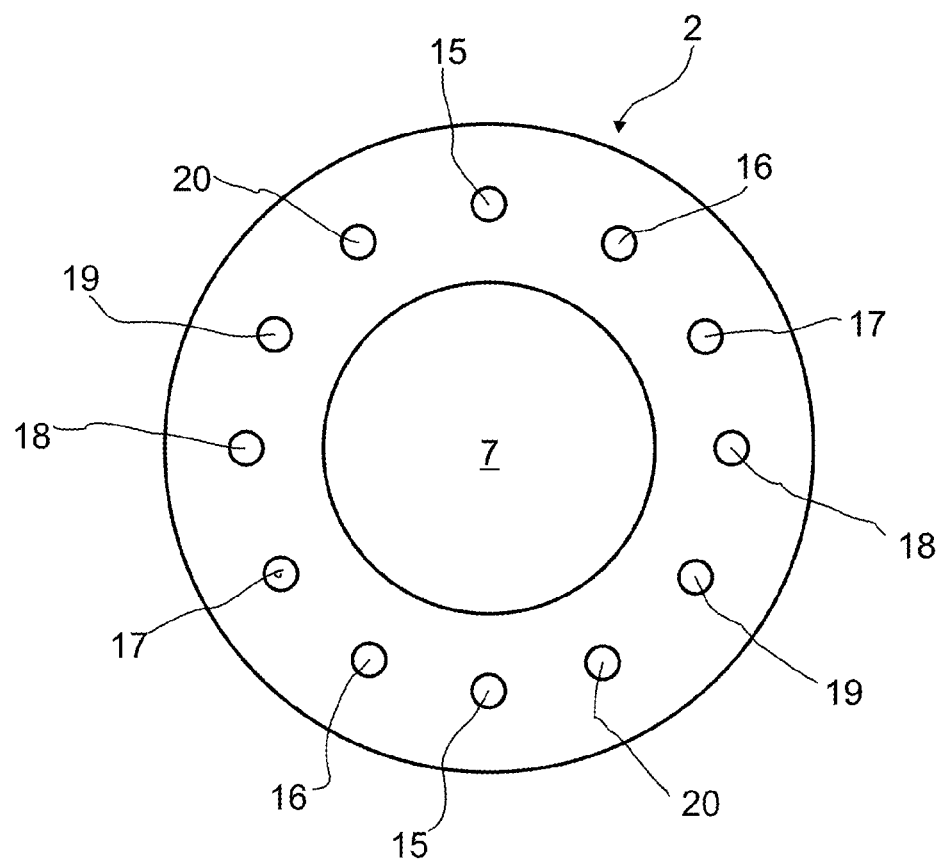
FIG. 2 shows the light-emitting unit of the device shown in FIG. 1.

The light-emitting unit 2 is shown in further detail in FIG. 2. The front view of the light-emitting unit 2 is ring-shaped, whereas a plurality of radiation sources like light-emitting diodes 2 is placed on the ring circumferentially, as shown in FIG. 2. In the example shown in FIG. 2 in total 12 light-emitting diodes 15 to 20 are provided, wherein two light-emitting diodes 15 emit light of a first excitation wavelength, two light-emitting diodes 16 emit radiation of a second wavelength, two light-emitting diodes 17 emit radiation of a third wavelength, two light-emitting diodes 18 emit radiation of a fourth wavelength, and two light-emitting diodes 19 emit radiation of a fifth wavelength, and two light-emitting diodes 20 emit radiation of a sixth wavelength. The first and second wavelengths are within the absorption band of a phenolic compound that is present in the plant 14 to be measured. The third to sixth wavelengths are outside the absorption band of such phenolic compound. In the present case, the first wavelength is 365 nm, the second wavelength is 395 nm, the third wavelength is 455 nm, the fourth wavelength is 470 nm, the fifth wavelength is 525 nm, and the sixth wavelength is 625 nm. However, it is mentioned that more or less than six different wavelengths may be used as excitation radiation. However, preferably, at least four different discrete excitation wavelengths are used. Furthermore, more than 12 light-emitting diodes 15 to 20 or less than 12 light-emitting diodes may be used.

Returning to FIG. 1, the mobile detection device 1 further comprises a control unit 4 connected to the light-emitting unit 2. The emission of the radiation by the light-emitting diodes 15 to 20 is controlled by control unit 4. In particular, control unit 4 can switch light-emitting diodes 15 to 20 on and off separately. Control unit 4 includes a pulse generator. By means of this pulse generator each light-emitting diode 15 to 20 may be switched on successively so that only one discrete excitation radiation wavelength is emitted at the same time.

The excitation radiation emitted by the light-emitting unit 2 induces fluorescence radiation that will be emitted by the leaves of the plant 14. Fluorescence radiation 5 that is emitted in the direction of the mobile detection device 1 is then detected by detector 6. Detector 6 comprises optics 7 for the incoming fluorescence radiation 5. The optics 7 is placed within the ring-shaped part of light-emitting unit 2, as shown in FIG. 2.

The light-emitting diodes 15 to 20 are switched on and off by control unit 4 rather fast. The measurement frequency is about 2 kHz so that the fluorescence radiation 3 is detected virtually continuously. Within the period of time in which all light-emitting diodes 15 to 20 are switched off it is possible to detect the influence of ambient radiation sources, which may then be compensated.

The detector 6 further comprises fiber optics 8 that guide the incoming fluorescence radiation 5 to a beam splitter 9. From beam splitter 9 the split light beam is guided to fiber optics 10-1 and 10-2. In fiber optics 10-1 a first optical filter 11-1 is arranged, and in fiber optics 10-2 a second optical filter 11-2 is arranged. Optical filters 11-1 and 11-2 only allow wavelengths to pass that relate to chlorophyll fluorescence radiation. In the present case, the first optical filter 11-1 only allows light of a wavelength of 685 nm to pass, and the second optical filter 11-2 only allows light of a wavelength of 735 nm to pass. However, the full width at half maximum of the filters 11-1 and 11-2 is 20 nm. The filtered light beams are transferred to a digitalizing unit 12. Digitalizing unit 12 may be a digital oscilloscope generating a digital signal based on the development and intensity of the light beam having a wavelength of 685 nm and the light beam having a wavelength of 735 nm. These digital data are transferred to an analyzing unit 13, which is also connected to control unit 4.

Figure 3:
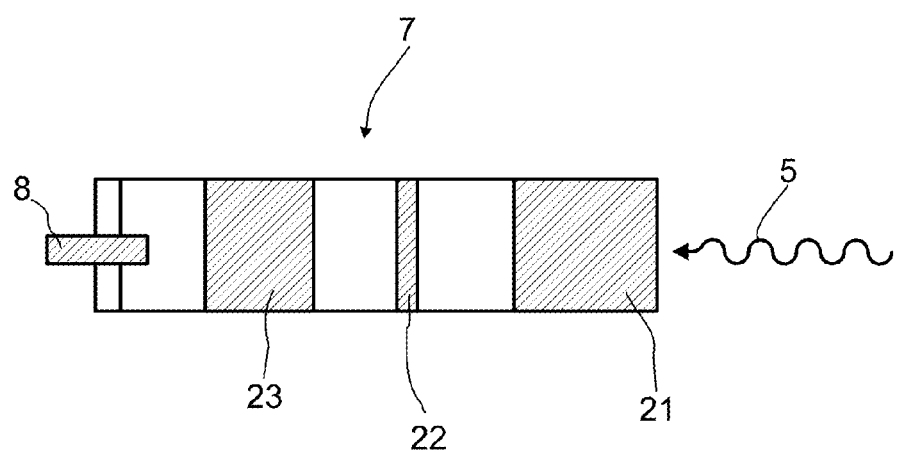
FIG. 3 shows the structure of the optics for incoming radiation of the detector of the device shown in FIG. 1.

With reference to FIG. 3, the optics 7 for incoming fluorescence radiation 5 is described in detail:

The incoming radiation 5 firstly passes camera lenses 21. After camera lenses 21, a glass long-pass filter 22 is arranged for wavelengths in the range of 645 nm to 1000 nm. Thereafter, a telecentric lens 23 is arranged. This telecentric lense 23 has its entrance pupil at infinity. Therefore, radiation 5 may be analyzed irrespective of the distance D between the mobile detection device 1 and the plant 14 that emits the fluorescence radiation 5.

From the telecentric lense 23 the light is guided to fiber optics 8.

In the following, further details of the mobile detection device 1 are described in connection with the description of an embodiment of the method of the present invention:

The mobile detection device 1 is placed on a tractor that drives over the field on which the plants 14 are planted. During the movement, the light-emitting unit 2 emits excitation radiation 3 to the plants 14. In particular, control unit 4 controls light-emitting diodes 15 to 20 such that excitation radiation 5 of different wavelengths is emitted in a cycle. This cycle is shown in FIG. 4:

In this case a variation of light-emitting unit 2 had been used. The light-emitting unit 2 does not comprise light-emitting diodes emitting radiation at six separate wavelengths, but light-emitting diodes emitting radiation at eight different wavelengths. The cycle begins with light-emitting diodes emitting radiation at a wavelength of 625 nm for a particular period of time. This light-emitting diode is then switched off, and another light-emitting diode is switched on, emitting radiation at a wavelength of 590 nm for the same period of time. Then, successively light-emitting diodes are switched on, emitting radiation at 525 nm, then at 470 nm, then at 455 nm, and then at 395 nm. Afterwards, all light-emitting diodes are switched off so that no excitation radiation is emitted for the same particular period of time. Then a light-emitting diode is switched on, emitting radiation at a wavelength of 365 nm, and finally the light-emitting diode emits radiation at 310 nm. Afterwards, the cycle is repeated. The control signals of control unit 4 are also transferred to analyzing unit 13 so that analyzing unit 13 can match the detected fluorescence radiation 5 with the wavelength of the excitation radiation 3.

The detector 6 detects the chlorophyll fluorescence radiation 3 from the plant 14 at two different wavelengths, namely at 685 nm and 735 nm.

Figure 4:
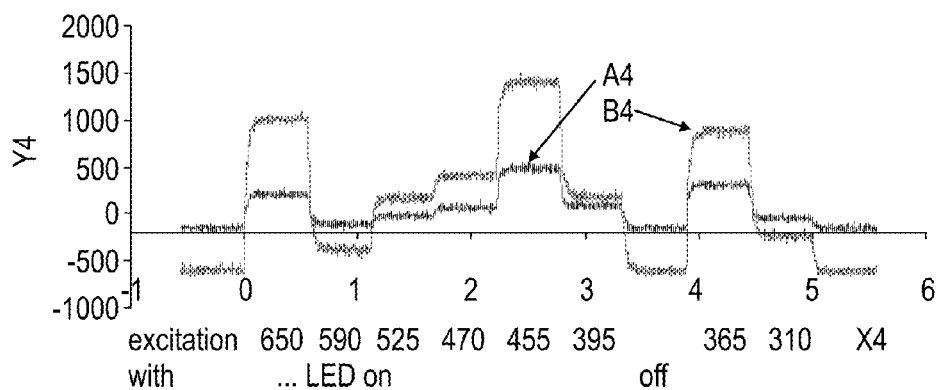
FIG. 4 shows an example of the signal detected by an embodiment of the detecting device.

In FIG. 4, graph A4 shows the detected chlorophyll fluorescence radiation 3 at 685 nm; graph B4 shows the detected chlorophyll fluorescence radiation 3 at 735 nm, wherein Y4 is the measured voltage U in mV, and X4 is the time t in ms.

The analyzing unit 13 then calculates a value for each detected fluorescence radiation wavelength. This value is indicative of the fungal infection of the plant 14 that has been irradiated with the excitation radiation 3. The value is dependent on the detected chlorophyll fluorescence radiation induced by excitation radiation of a first excitation wavelength and the detected chlorophyll fluorescence radiation induced by excitation radiation of a second excitation wavelength, wherein the first excitation wavelength is within the absorption band of a phenolic compound, and the second excitation wavelength is outside the absorption band of a phenolic compound. In the present case, the value is calculated as follows:

$$V = \frac{F685exc625}{F685exc395}$$

wherein F685exc625 is the signal of the chlorophyll fluorescence radiation 5 at the wavelength of 685 nm, induced by excitation radiation 3 at the wavelength of 625 nm, and F685exc395 is the signal of the chlorophyll fluorescence radiation 5 detected at the wavelength of 685 nm induced by excitation radiation at the wavelength of 395 nm. Therefore, the value V has been normalized with respect to the excitation radiation 3 with red light at 625 nm so that the value V is independent of the measurement distance D, the geometry of the plant 14, and the chlorophyll content.

FIG. 4 shows the detected chlorophyll fluorescence radiation at 685 nm (graph A4) and the detected chlorophyll fluorescence radiation at 735 nm (graph B4) for different excitation wavelengths.

Figure 5:
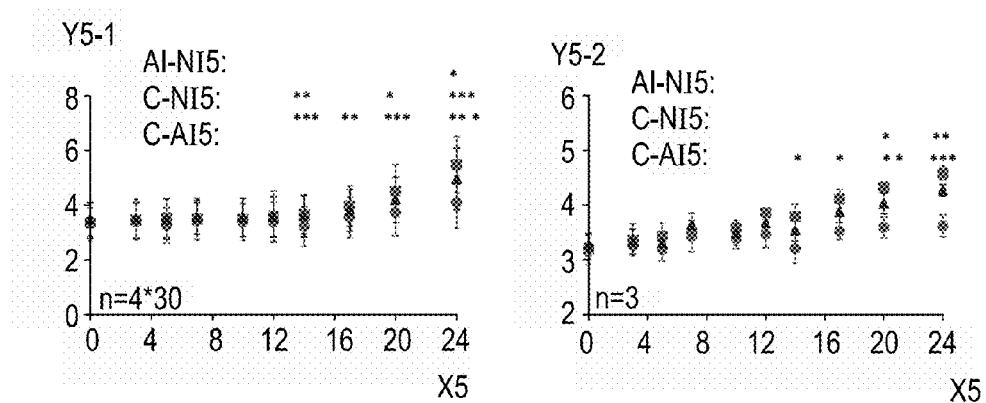
FIG. 5 shows a diagram showing the determined fluorescence quotient and a diagram showing the content of polyphenol of the corresponding plants.

FIG. 5 shows the development of the fluorescence coefficient, namely the value V, for chlorophyll fluorescence radiation 5 at the wavelength of 685 nm after a fungal infection event.

In FIG. 5, C5 designates the control value (healthy plants), AI5 designates the data for artificial inoculation with *Septoria tritici*, NI5 designates the data for natural inoculation. Further, X5 designates the day after an inoculation event, Y5-1 designates the fluorescence quotient V, Y5-2 designates the content of polyphenol (mg/g DM), AI-NI5 designates the difference between AI5 and NI5, C-NI5 designates the difference between C5 and NI5, and C-AI5 designates the difference between C5 and AI5. Finally, * designates the level of significance for a p-value<0.05;  the level of significance for a p-value<0.01, and * the level of significance for a p-value<0.001.

Therefore, in the left diagram, the data show control values for healthy plants as well as values for an artificial and a natural inoculation. Furthermore, different levels of significance are shown. In the right diagram, the corresponding actual content of polyphenol is shown. In both diagrams a one-way ANOVA has been carried out with subsequent post-hoc tests according to Tukey. The one-way ANOVA is a comparative mean of normally distributed data with homogeneity of variance. The significances between the three variants are determined according to Tukey as is generally known.

Figure 6:
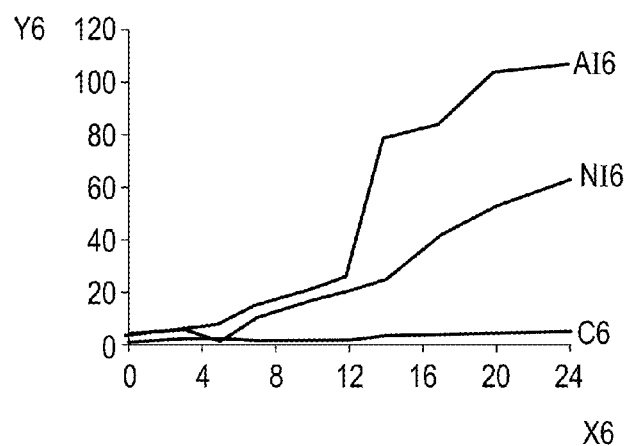
FIG. 6 shows the development of the fungal DNA as determined by PCR.

FIG. 6 shows the concentration of fungal DNA in wheat leaves of an outdoor trial.

In FIG. 6, X6 designates the day after the inoculation event, Y6 designates the fungal DNA (estimated with qPCR as relative quotient set to 1 on day 0), C6 designates the control values (healthy plants), NI6 designates the natural inoculation, and AI6 designates the artificial inoculation with septoria tritici. In this trial three variants were designed: Control plants applied with fungicides to keep healthy plants, artificial inoculated plants sprayed with spores of septoria tritici and natural inoculated plants with no special treatment. The fungal DNA was measured by means of qPCR and a relative quotient was calculated by setting the measured value on day 0 to 1.

It can be derived from FIGS. 5 and 6 that the mobile detection device 1 can determine an infection with *s. tritici* only two weeks after the infection, compared with plants 14 that have not been infected. Furthermore, the determined value for the fungal infection makes a quantitative verification possible, because the value shows how strong the infection is. The strongness of the infection was adjusted by the infection intensity, time period, and it was referenced to quantitative verifications based on HPLC measurements for phenolic compounds and qPCR measurements for fungal DNA. Moreover, measurements carried out in a climatic chamber with *p. recondite* show one week after the first infection distinguishable detection signals with respect to plants that have not been infected.

Furthermore, as mentioned above, the chlorophyll fluorescence radiation 5 is detected for several wavelengths of excitation radiation 3. The analysis of the chlorophyll fluorescence radiation 5 for different excitation radiations can improve the significance of the detected differences between plants 14 that are infected relative to plants 14 that are not infected. In fact, the significance can be improved, although, in addition, fluorescence radiation 5 is analyzed that is induced by excitation radiation 3 of wavelengths that are outside the absorption bands of phenolic compounds. Therefore, the excitation radiation 3 of wavelengths outside the absorption band of phenolic compounds may be used not only for normalization of the value V, but also for improving the significance of the determined value.

Figure 7:
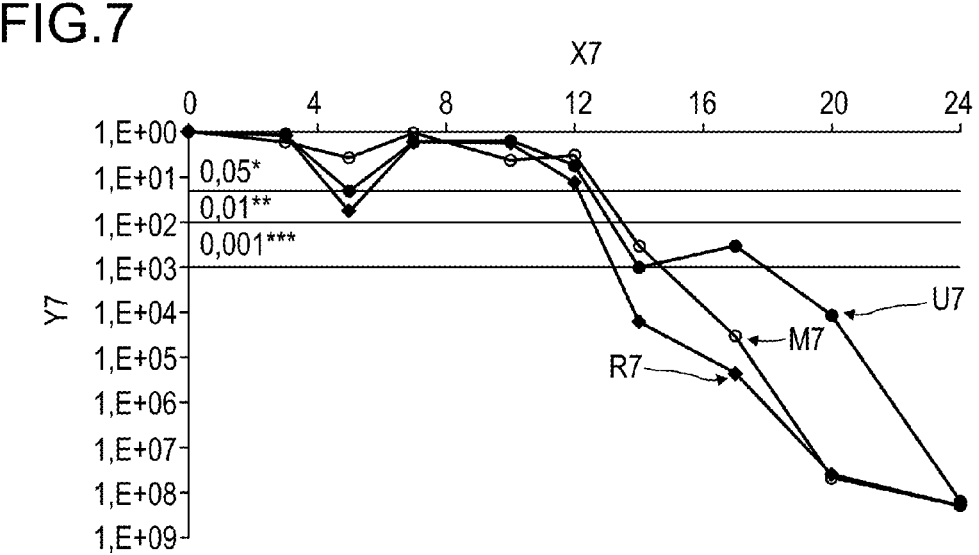
FIG. 7 shows an example of an analysis of the measurements with respect to significance.

FIG. 7 shows the development of the p-value for the significance level relative to the elapsed time after infection. A lower p-value means a higher significance for the differentiation between infected and non-infected plants 14. If the p-value is lower than 0.001, the determined value is highly significant.

In FIG. 7, X7 designates the day after the inoculation event, Y7 designates the p-value (logarithmic scale), * designates that the p-value is significant,  that that the p-value is very significant, and * that the p-value is highly significant.

The graph M7 designates the multivariate analysis. Graph M7 shows the p-value for an analysis using six different wavelengths for the excitation radiation 3. For example, a detector 6 as shown in FIG. 2 may be used for such measurements. Furthermore, graph U7 designates the univariat analysis. In this case only excitation radiation 3 of the wavelength of 395 nm has been used. It can be seen from FIG. 7 that in the case of the analysis of six different wavelengths for the excitation radiation 3, the p-value is highly significant earlier than in the case of the analysis of only one wavelength for the excitation radiation 3. It is mentioned that in any case normalization has been used based on excitation radiation 3 with red light (625 nm). Finally, the graph R7 designates the univariat analysis for control. In this case a control stripe with healthy plants has been used for calculating the difference between healthy and infected plants on each plot.

It is assumed that after a fungal infection of a plant 14 the following happens: The fungus infiltrates the leaves of the plant 14. In response to this infiltration the content of phenolic compounds in the leaves of the plant 14 increases. This increase of the content of the phenolic compounds can be measured according to the method of the present invention by induced chlorophyll fluorescence radiation by an increase of the values V calculated by analyzing unit 13, as described above.

Moreover, as described above, the chlorophyll fluorescence radiation 5 is detected at two separate wavelengths. If the signals detected at these different wavelengths are analyzed in analyzing unit 13 the ratio of the signals may be used for determining the chlorophyll concentration in the plant tissue. In fact, the chlorophyll concentration may be determined as self-absorption occurs in the closely packed chlorophyll layer of the leaf of the plant 14 and the shift of the chlorophyll fluorescence radiation 5 in the direction to longer wavelengths relative to absorption. Therefore, the chlorophyll fluorescence radiation 5 having a longer wavelength of 735 nm, increases relative to the chlorophyll fluorescence radiation at a shorter wavelength of 685 nm. Therefore, the ratio of the chlorophyll fluorescence radiation 5 at the two different wavelengths may be used for the detection of the reduction of the chlorophyll concentration in the plant tissue in a later phase of the fungal infection.

It is mentioned that the present invention is not limited to the above-described embodiment. For example, the first excitation wavelength may be within the absorption band of a specific compound whose content in the plant is affected by a fungal infection instead of the phenolic compound. Likewise, the second excitation wavelength may be used that is outside the absorption band of this compound.

According to another embodiment, the radiation sources may illuminate electromagnetic radiation to the plant and filter this illuminated electromagnetic radiation to the first and second excitation wavelengths. Alternatively, a hyperspectral sensor may be utilized instead of said filtering and only the bands with the required wavelength may be used for the analysis.

Furthermore, according to another embodiment, the detection device 1 is not fixed to a tractor but to a drone, an aeroplane or the like. Moreover, the detection device 1 may not be mobile but fixed to the field.

LIST OF REFERENCE SIGNS 1 mobile detection device
2 light-emitting unit
3 excitation radiation
4 control unit
5 fluorescence radiation
6 detector
7 optics for incoming radiation
8 fiber optics
9 beam splitter
10-1, 10-2 fiber optics
11-1, 11-2 first and second optical filter
12 digitalizing unit
13 analyzing unit
14 plant
15 first light-emitting diodes
16 second light-emitting diodes
17 third light-emitting diodes
18 fourth light-emitting diodes
19 fifth light-emitting diodes
20 sixth light-emitting diodes
21 camera lenses
22 long-pass filter
23 telecentric lense

The invention claimed is:

1. A method for determining a fungal infection affecting the content of a phenolic compound of a plant, comprising: determining a change in the content of the phenolic compound of the plant comprising:
   providing an excitation radiation by one or more radiation sources to the plant, said radiation comprising first excitation wavelengths being within the absorption band of the phenolic compound and second excitation wavelengths being outside the absorption band of said phenolic compound, thereby inducing chlorophyll fluorescence;
   detecting only the chlorophyll fluorescence radiation from the plant; and
   obtaining a variation of a value being indicative for the fungal infection of the plant, said value is dependent from the detected chlorophyll fluorescence radiation induced by excitation radiation of the first excitation wavelengths and the detected chlorophyll fluorescence radiation induced by excitation radiation of the second excitation wavelengths.

2. The method of claim 1, wherein said providing excitation radiation includes illuminating electromagnetic radiation to the plant and filtering said illuminated electromagnetic radiation to said first excitation wavelengths being within the absorption band of the compound whose content in the plant is affected by the fungal infection and to said second excitation wavelengths being outside the absorption band of said compound.

3. The method of claim 1, wherein the value is dependent from the ratio of the detected chlorophyll fluorescence radiation induced by excitation radiation of the first excitation wavelengths and the detected chlorophyll fluorescence radiation induced by excitation radiation of the second excitation wavelengths.

4. The method of claim 1, wherein said first excitation wavelengths are in a range from 200 nm to 400 nm and said second excitation wavelengths are in a range from 450 nm to 650 nm.

5. The method of claim 4, wherein said first measurement wavelength is between 670 nm and 700 nm and said second measurement wavelength is between 715 nm and 745 nm.

6. The method of claim 1, wherein the chlorophyll fluorescence radiation from the plant is detected for at least a first and second measurement wavelengths, said first and second measurement wavelengths being different.

7. The method of claim 6, wherein analyzing the detected chlorophyll fluorescence radiation at the first measurement wavelength relative to the detected chlorophyll fluorescence radiation at the second measurement wavelength thereby determining the reduction of chlorophyll concentration in the plant tissue.

8. The method of claim 1, wherein said excitation radiation comprises at least four different discrete excitation wavelengths and wherein said value is dependent from the detected chlorophyll fluorescence radiations induced by excitation radiation of said at least four discrete excitation wavelengths.

9. The method of claim 1, wherein the excitation radiation radiates one or more leaves of the plant.

10. The method of claim 1, wherein the plant is irradiated from a distance larger than 10 cm and less than 10 m.

11. A detecting device for determining a fungal infection affecting the content of a phenolic compound of a plant, comprising:

one or more radiation sources for emitting providing excitation radiation to the plant, said radiation comprising first excitation wavelengths being within the absorption band of the phenolic compound and second excitation wavelengths being outside the absorption band of said phenolic compound, thereby inducing chlorophyll fluorescence;

a detector comprising one or more optical filters that only allow wavelengths to pass that relate chlorophyll fluorescence radiation for detecting chlorophyll fluorescence radiation from the plant; and an analyzing unit coupled with the detector for obtaining a variation of a value being indicative for the fungal infection of the plant, said analyzing unit is adapted to calculate said value in dependence from the detected chlorophyll fluorescence radiation induced by excitation radiation of the first excitation wavelengths and the detected chlorophyll fluorescence radiation induced by excitation radiation of the second excitation wavelengths.

12. The detecting device of claim 11, wherein the detector comprises one or more optical elements having an entrance pupil at infinity.

13. The detecting device of claim 11, wherein said optical elements are arranged to form a telecentric lense system.

14. The detecting device of claim 11, wherein the radiation sources are light-emitting diodes.

15. The detecting device of claim 14, wherein the light-emitting diodes emit at least four different discrete excitation wavelengths.

16. The detecting device of claim 11, wherein the detector is adapted to detect the chlorophyll fluorescence radiation for at least a first and second measurement wavelengths, said first and second measurement wavelengths being different.

17. The detecting device of claim 11, wherein said detecting device is a mobile detecting device.

18. An apparatus for determining a fungal infection of a plant comprising the detecting device of claim 11.

19. The apparatus of claim 18, wherein said apparatus is a vehicle or a satellite.

20. The apparatus of claim 18, wherein said apparatus is fixed on the plant field.

* * * * *

UNITED STATES PATENT AND TRADEMARK OFFICE
CERTIFICATE OF CORRECTION

PATENT NO. : 9,921,162 B2
APPLICATION NO. : 15/105056
DATED : March 20, 2018
INVENTOR(S) : Ylva Tischler et al.

It is certified that error appears in the above-identified patent and that said Letters Patent is hereby corrected as shown below:

In the Claims

Claim 11, Column 14, Line 1, please delete the word "emitting"

Claim 11, Column 14, Line 9, after the word "relate" please insert the word --to--

Signed and Sealed this
Tenth Day of December, 2019

Andrei Iancu
*Director of the United States Patent and Trademark Office*